(12) United States Patent
Betzer et al.

(10) Patent No.: US 7,399,880 B2
(45) Date of Patent: Jul. 15, 2008

(54) PROCESS FOR REMOVING FARNESOL FROM MIXTURES WITH ALPHA-BISABOLOL

(75) Inventors: Marcus Betzer, Holzminden (DE); Walter Kuhn, Holzminden (DE); Burghard Wilkening, Bodenwerder (DE); Dietmar Schatkowski, Stadtoldendorf (DE); Oskar Koch, Göttingen (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 11/553,770

(22) Filed: Oct. 27, 2006

(65) Prior Publication Data
US 2007/0100160 A1  May 3, 2007

(30) Foreign Application Priority Data
Oct. 29, 2005  (DE)  ............. 10 2005 051 903

(51) Int. Cl.
*C07C 67/40* (2006.01)
*C07C 67/02* (2006.01)

(52) U.S. Cl. .................. 560/204; 560/162; 562/5
(58) Field of Classification Search .......... 560/31, 560/162, 204, 239; 562/5; 568/319
See application file for complete search history.

(56) References Cited

OTHER PUBLICATIONS

Brieger, G. et al., The systnesis of trans, trans-alpha-farnesene, 1969, Journal of Organic Chemistry, vol., No. 12, pp. 3789.*

* cited by examiner

*Primary Examiner*—Yvonne Eyler
*Assistant Examiner*—Yate' K Cutliff
(74) *Attorney, Agent, or Firm*—Roylance, Abrams, Berdo & Goodman, L.L.P.

(57) ABSTRACT

Process for esterification of farnesol in an initial mixture comprising alpha-bisabolol, farnesol and optionally other components, with the following steps:
1. Preparation or production of the initial mixture,
2. Adding (i) a transesterification catalyst and (ii) one or more compounds of formula (B)

$$R^2\text{-}[Y]_n\text{-}CO_2R^1 \tag{B}$$

in which the following applies:
$R^1$ stands for an alkyl residue with 1 to 12 C atoms;
$R^2$ stands for hydrogen, an alkyl residue with 1 to 20 C atoms, a cycloalkyl residue with 5 to 20 C atoms, an aryl residue with 6 to 20 C atoms or a heteroaryl residue with 5 to 20 C atoms; and
Y stands for $CH_2$, $CH(Me)$, $CH(Et)$, $C(Me)_2$, $CH_2$—$CH(Me)$, $CH(Me)$-$CH_2$ or $CH_2$—$CH(Me)$-$CH_2$ and n stands for a whole number from 0 to 6;
or
$R^2$ stands for a group $CO_2R^3$, $R^3$ standing for an alkyl residue with 1 to 12 C atoms; and
Y stands for $CH_2$, $CH(Me)$, $CH(Et)$, $C(Me)_2$, $CH_2$—$CH(Me)$, $CH(Me)$-$CH_2$ or $CH_2$—$CH(Me)$-$CH_2$ and n stands for a whole number from 0 to 8, or
Y stands for an optionally substituted phenyl or naphthyl ring with a total of at most four substituents on the ring, n=1 applying.

14 Claims, No Drawings

PROCESS FOR REMOVING FARNESOL FROM MIXTURES WITH ALPHA-BISABOLOL

This invention relates to a process for reducing the proportion of farnesol in mixtures containing farnesol and alpha-bisabolol. Chamomile oil is defined as the essential oil from the flowerheads of the true chamomile, Chamomilla recutita (L) Rauschert. It is cited in the supplement to the German Pharmacopeia as "oleum chamomillae". True chamomile is one of the most common medicinal plants. The composition of chamomile oil depends on the origin and type of drug material used. It is moreover influenced by the distillation conditions of steam distillation. Chamomile itself contains a large amount of mono- and sesquiterpenes, the therapeutically relevant sesquiterpenes quantitatively predominating. The most important components of the essential oil are chamazulene which gives it its deep-blue color, (−)-alpha-bisabolol, bisabolol oxide A, bisabolol oxide B, bisabolone oxide A, cis- and trans-spiroether and farnesene. Chamomile blossoms of varied origin also have distinct differences in their composition. While chamomile of the bisabolol type in its natural occurrence is limited to northeast Spain, the bisabolol oxide A-type is common over all of central, southern and eastern Europe and Egypt. The less common bisabolone oxide A-type is known from Albania and Turkey.

In the assessment of the therapeutic effectiveness of chamomile extract preparations, (−)-alpha-bisabolol assumes a dominant position since in its antiphlogistic action it is greatly superior to the action of (+)-alpha-bisabolol, the synthetic bisabolol racemate and bisabolol oxides A and B.

While systematic cultivation of medicinal plants and spice plants is growing more and more important due to increased demand for "renewable resources", limited natural resources have led at the same time to the search for and development of processes for obtaining synthetic products.

Synthetic "alpha-bisabolol" conventionally represents a diastereomer racemate of the same proportions of (+/−)-alpha-bisabolol and (+/−)-epi-alpha-bisabolol. All four enantiomers have been found in nature.

(−)-(4S,8R)-alpha-epi-bisabolol is a natural component of Citrus bergamia RISSO essential oil [Helv. Chim. Acta 1986, 69, 698] and its enantiomer (+)-(4R,8S)-alpha-epi-bisabolol has been isolated from various Abies and Picea species [Aust. J. Chem. 1982, 42, 2021], while (+)-(4R,8R)-alpha-bisabolol is a component of Atalantia monophylla corren oils [Aust. J. Chem. 1989, 42, 2021; Tetrahedron 1981, 37 (suppl.) and its enantiomer (−)-(4S,8S)-alpha-bisabolol is one of the main components of German chamomile [Parf Cosm. Aromes 1984, 57, 56].

(−)-(4S,8S)-alpha-bisabolol is produced on a large industrial scale for numerous applications in the cosmetics and perfume sector, for example for use in protective creams, lotions, deodorants, etc., and especially due to its antiinflammatory, bacteriostatic and antimycotic properties [Planta Med. 1990, 56, 456].

For a long time the absolute configuration of the individual enantiomers of alpha-bisabolol had not been clearly determined. But J. Org. Chem. 1993, 58, 5528, then finally describes a process for producing the individual isomers by enantioselective hydrolysis, proceeding from (4S,8RS)- and (4R,8RS)-8,9-epoxy-p-menth-1-ene.

Based on its described action, there is a continuing demand for (+), (−) and (+/−)-alpha-bisabolol and/or (+)-epi, (−)-epi and (+/−)-epi-alpha-bisabolol, i.e., for compounds of formula A

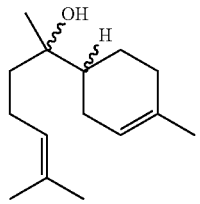

in which the jagged lines are on the pertinent C atom independently of one another for an S or R configuration. Thus a host of processes and methods for producing bisabolol proceeding from nerolidol have been described in the past.

The first catalytic cyclization of farnesol was described in 1913 when it was observed that in carrying out a reaction in the presence of potassium hydrogen sulfate, in addition to the expected hydrocarbons also some mono- and bicyclic compounds were found [Chem. Ber. 46, 4024 (1913)]. Later works then identified these cyclic compounds as compounds of the bisabolene and cadalene class.

In 1925 a careful study was done for the first time in which, proceeding from nerolidol by acid catalysis, products such as farnesene, bisabolene and bisabolol were obtained [Helv. Chim. Acta 8, 259 (1925)]. It was shown in particular that nerolidol yields a mixture which comprises bisabolol and farnesol by the addition of acetane hydride, subsequent conversion with acetic acid/sulfuric acid or formic acid at room temperature and subsequent saponification.

In 1968 Gutsche [Tetrahedron 24, 859] reported on the acid-catalyzed cyclization of farnesol and nerolidol. Proceeding from farnesol or nerolidol first by conversion with formic acid the corresponding formiates were obtained which were then saponified in a second step to the alcohols. According to this procedure however mixtures of substances are formed which in addition to bisabolol also contain farnesol. Subsequent distillative purification into highly enriched bisabolol is difficult, especially because alpha-bisabolol and cis, cis-farnesol have almost identical boiling points and mixtures of substances obtained according to the described procedure contain up to 10% cis, cis-farnesol.

Other syntheses of bisabolol have been described by Ruzicka et al. [Helv. Chim. Acta 15, 3, (1932)] and by Manjarrez et al. [J. Org. Chem. 31, 348, (1966)]. Acid-catalyzed cyclization in the presence of formic acid in pentane or $AlCl_3$ in ether [Tetrahedron Lett. 1972, 2455], $KHSO_4$ [J. Org. Chem. 34, 3789, (1969)] and $BF_3$-etherate in methylene chloride [Chem. Lett. 1972, 263] has likewise been described.

Uneyama et al. report on the electrochemical method of synthesis [Chem. Lett. 1984, 529], in this connection also the production of DL bisabolol from DL nerolidol is reported. While the above described process proceeding from nerolidol rarely led to bisabolol yields exceeding 30%, yields up to 52% were obtained with electrochemical processes.

WO 2004/033401 describes a process for producing alpha-bisabolol, in which nerolidol is converted in a step with a mixture consisting of a ketone, a sulfonic acid, and perchloric acid. This process is characterized among others by its leading to especially pure alpha-bisabolol and especially the (+), (−) or (+/−) farnesol which forms in the above described processes as a byproduct in a yield of up to 40% being formed only in comparatively small concentrations.

It is common to the processes known from the prior art for producing bisabolol that generally farnesols in more or less large amounts are also formed. But the presence of farnesols in product mixtures in addition to bisabolol is undesirable because an allergenic potential is ascribed to farnesols which makes especially use in cosmetic products problematic. In the development of cosmetic products specifically not only are the cosmetic properties of interest, but the safety of the substances contained relative to man and the environment must be considered to the greatest extent possible. Especially improved toxicological, ecotoxicological and dermatological properties contribute to the value of a new product. From a dermatological standpoint a cosmetic product should not have any skin-irritating, sensitizing and/or photosensitizing properties. In this respect the presence of farnesol in cosmetic products is being increasingly perceived as problematic. The IFRA (International Fragrance Association) has classified farnesol and a series of other mono- and sesquiterpenes in subcategory 2 which contains products with an allergenic potential which is observed with less frequency but still in a significantly large number of probands. The allowable concentrations of use of the compounds contained in subcategory 2 have been limited in various product categories.

It has already been mentioned in the foregoing that the distillative separation of alpha-bisabolol and farnesol is especially difficult because alpha-bisabolol and cis, cis-farnesol have almost identical boiling points. If product mixtures which comprise also a notable proportion of farnesols in addition to the desired alpha-bisabolol are however to be distillatively separated, to achieve at least a certain success long thermal loading is necessary such that secondary reactions and especially decomposition of the compounds synthesized beforehand occur to a high degree.

It was therefore the object of this invention to devise a process which enables or facilitates the separation of alpha-bisabolol and farnesol(s) so that overall a product or product mixture which is largely or essentially free of farnesol(s) can be obtained.

Preferably a product mixture produced according to the process should contain a proportion of at least 90% by weight bisabolol and a portion of farnesol of less than 0.5% by weight.

This object is achieved as claimed in the invention by a process for esterification of farnesol by means of transesterification in an initial mixture comprising alpha-bisabolol, farnesol and optionally other components, with the following steps:
1. Preparation or production of the initial mixture (that is, comprising alpha-bisabolol, farnesol and optionally other components),
2. Adding (i) a transesterification catalyst and (ii) one or more compounds of formula B

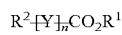    B in which the following applies:
$R^1$ stands for an alkyl residue with 1 to 12 C atoms;
$R^2$ stands for hydrogen, an alkyl residue with 1 to 20 C atoms, a cycloalkyl residue with 5 to 20 C atoms, an aryl residue with 6 to 20 C atoms or a heteroaryl residue with 5 to 20 C atoms; and
Y stands for $CH_2$, CH(Me), CH(Et), $C(Me)_2$, $CH_2$—CH(Me), CH(Me)-$CH_2$ or $CH_2$—CH(Me)-$CH_2$ and n stands for a whole number from 0 to 6;
or
$R^2$ stands for a group $CO_2R^3$, $R^3$ standing for an alkyl residue with 1 to 12 C atoms; and Y stands for $CH_2$, CH(Me), CH(Et), $C(Me)_2$, $CH_2$—CH(Me), CH(Me)-$CH_2$ or $CH_2$—CH(Me)-$CH_2$ and n stands for a whole number from 0 to 8, or
Y stands for an optionally substituted phenyl or naphthyl ring with a total of at most four substituents on the ring, n=1 applying.

In this context the abbreviations Me and Et have the conventional meaning: Me=methyl and Et=ethyl.

The respective alkyl residues can be branched or straight-chain.

In this connection the mixture used (initial mixture) comprising alpha-bisabolol, farnesol and optionally other components is produced according to one of the above discussed processes, preferably according to the process claimed in WO 2004/033401. Alternative processes for producing alpha-bisabolol, especially those based on nerolidol as the educt, can likewise be used to produce initial mixtures comprising bisabolol, farnesol and optionally other components.

The concept of "alpha-bisabolol" within the framework of the text encompasses (+)-alpha-bisabolol, (−)-alpha-bisabolol, (+)-epi-alpha-bisabolol and (−)-epi-alpha-bisabolol and mixtures of two, three or all of the aforementioned isomers of alpha-bisabolol. In particular, the concept of "alpha-bisabolol" encompasses racemic mixtures of (+/−)-alpha-bisabolol and (+/−)-epi-alpha-bisabolol.

The invention is based on the surprising finding that the farnesol present in the mixture (comprising alpha-bisabolol, farnesol and optionally other components) in the presence of a transesterification catalyst and one or more compounds of formula B is reacted into a farnesyl ester, while the alpha-bisabolol present at the same time in the mixture is not esterified at all or at the most to an insignificant extent.

The compound(s) of formula B have surprisingly proven to be extremely selective transesterification or esterification reagents which when added to a mixture of alpha-bisabolol and farnesol highly selectively esterify the farnesol, while the alpha-bisabolol is at the most esterified to a small extent or not at all.

In the process as claimed in the invention the amount of one or more compounds of formula B which were used (as indicated above) is preferably sufficient to esterify the amount of farnesol present in the mixture. In this connection, consideration should be given to the fact that in addition to alpha-bisabolol and farnesol there may be still other alcohols in the mixture, for example educt material from bisabolol synthesis, that is, especially nerolidol. Nerolidol also remains essentially unaffected in the transesterification reaction.

In particular, when the proportion of other alcohols (besides alpha-bisabolol and farnesol) is only small, the molar ratio of farnesol to the total amount of compound or compound(s) of formula B is preferably in the range from 1:1 to 1:10, preferably in the range from 1:1.1 to 1:5. With these molar ratios generally the farnesol present in the mixture (comprising alpha-bisabolol, farnesol and optionally other components) can be completely esterified with high selectivity.

The conversion of a mixture comprising alpha-bisabolol and farnesol is shown in simplified form in the following diagram 1. The illustrated isomers of alpha-bisabolol or farnesol should be understood here simply as examples.

Diagram 1

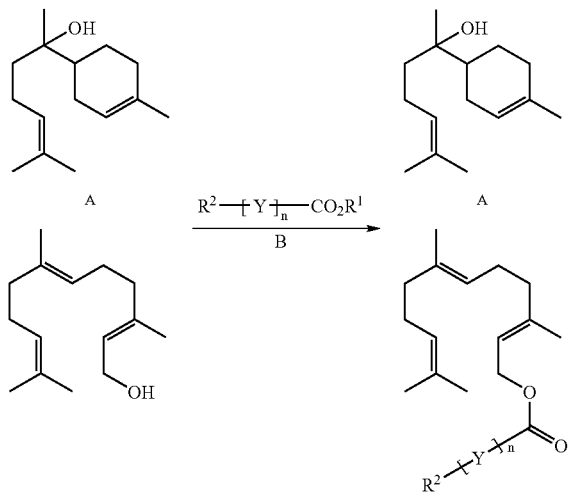

Depending on the production method, the initial mixtures to be treated comprise in addition to alpha-bisabolol and farnesol one or more of the following substances: nerolidol; elimination products of bisabolol (bisabolenes); elimination products of farnesol (farnesenes); etherification products of farnesol (difarnesyl ether); rearrangement products of bisabolol and/or of farnesol and/or of nerolidol; sesquiterpenes and sesquiterpene alcohols such as khusiol, germacradienol, elemol, and eudesmol.

In the process as claimed in the invention, monocarboxylic acid alkyl esters or dicarboxylic acid dialkyl esters of formula B are used. The amount of compound(s) of formula B used is preferably chosen such that at least 1 molar equivalent of the compound(s) of formula B is used per molar amount of farnesol present in the initial mixture (comprising alpha-bisabolol, farnesol and optionally other components). The greater the molar excess of compound(s) of formula B, the more quickly the transesterification reaction with farnesol proceeds and the smaller the farnesol content in the alpha-bisabolol (after purification operations such as for example distillation). For reasons of process economy the molar ratio of farnesol to the total amount of compound(s) of formula B is especially preferably in the range from 1:1.2 to 1:3.5.

Preferably $R^1$ stands for an alkyl residue with 1 to 4 carbon atoms, especially preferably methyl, ethyl, n-propyl, or iso-propyl.

In the case in which the compound B constitutes a monocarboxylic acid alkyl ester, $R^2$ preferably stands for hydrogen, an alkyl residue with 3 to 8 C atoms or an aryl residue with 6 to 10 C atoms, especially preferably an aryl residue with 6 to 8 C atoms; and/or Y stands for $CH_2$, $CH(Me)$, $CH_2$—$CH(Me)$, $CH(Me)$-$CH_2$ or $CH_2$—$CH(Me)$-$CH_2$ and n stands for a whole number from 0 to 6, in turn preferably the monocarboxylic acid part of the monocarboxylic acid alkyl ester of formula B having a total number of C atoms of at least 5 and at most 12, preferably of at least 6 and at most 10.

Especially preferable monocarboxylic acid alkyl esters of formula B are: benzoic acid-$C_1$-$C_4$-ester, especially benzoic acid methyl ester and benzoic acid ethyl ester.

In the case in which compound B constitutes a dicarboxylic acid dialkyl ester, $R^2$ preferably stands for a group $CO_2R^3$, in which $R^3$ stands for an alkyl residue with 1 to 4 C atoms, especially methyl, ethyl, n-propyl, or iso-propyl, and furthermore preferably has the same meaning as $R^1$; and/or Y stands for $CH_2$ and n stands for a whole number from 0 to 6, preferably a whole number from 2 to 5, or Y stands for $CH_2$—$CH(Me)$, $CH(Me)$-$CH_2$ or $CH_2$—$CH(Me)$-$CH_2$ and n=0, 1 or 2; or Y stands for a phenyl or naphthyl ring, n being equal to 1.

In the case of the alkyldicarboxylic acid dialkyl ester of formula B in turn those are preferred in which the alkyldicarboxylic part of the dicarboxylic acid alkyl ester of formula B has a total number of C atoms of at least 3 and at most 12, preferably of at least 4 and at most 10.

Especially preferred alkyldicarboxylic acid dialkyl esters of formula B are: succinic acid-$C_1$-$C_4$-ester, especially succinic acid ethyl ester, succinic acid isopropyl ester, adipinic acid-$C_1$-$C_4$-ester, especially adipinic acid ethyl ester, adipinic acid isopropyl ester, glutaric acid-$C_1$-$C_4$-ester, especially glutaric acid acid ethyl ester, glutaric acid isopropyl ester, 3-methylglutaric acid-$C_1$-$C_4$-ester, especially 3-methylglutaric acid acid ethyl ester, 3-methylglutaric acid isopropyl ester, subaric acid-$C_1$-$C_4$-ester, azelaic acid-$C_1$-$C_4$-ester.

In the case of aryldicarboxylic acid dialkyl esters of formula B, those in which the aryldicarboxylic acid part of the dicarboxylic acid dialkyl ester of formula B has a total number of C-atoms of at least 8 and at most 12 are in turn preferred.

Especially preferred aryldicarboxylic acid dialkyl esters of formula B are: phthalic acid diethyl ester, phthalic acid diisopropyl ester, phthalic acid dibutyl ester, terephthalic acid diethyl ester, 2,6-naphthalinic dicarboxylic acid diethyl ester, 2,6-naphthalinic dicarboxylic acid di-2-ethylhexylester.

Preferably the compound(s) to be used as claimed in the invention of formula B does/do not have (almost) the same boiling point as the alpha-bisabolol (about 287° C. at 1013 mbar).

In one preferred embodiment of this invention the compound(s) of formula B has or have a boiling point of at most 275° C., preferably one of at most 260° C., each at 1013 mbar. In this way it is possible to advantageously isolate the purified alpha-bisabolol in a form economical for the process. After completion of the transesterification reaction, the excess amount of compound(s) of formula B which may be present can be distilled off, followed by alpha-bisabolol, the esterified farnesol and other esterified alcohols originating from the original mixture remaining in the bottom.

The amount of transesterification catalyst used is preferably chosen such that relative to the molar amount of farnesol present in the initial mixture (comprising alpha-bisabolol, farnesol and optionally other components), 0.001 to 0.5 molar equivalents of the transesterification catalyst are used, preferably 0.01 to 0.1 molar equivalents.

Preferred transesterification catalysts are titanium alcoholates $Ti(OR^i)_4$ and zirconium alcoholates $Zr(OR^i)_4$, the residue $R^i$ being a branched or straight-chain alkyl residue with 1 to 12 C atoms. Especially preferable transesterification catalysts are ($Ti(OR^i)_4$ and $Zr(OR^i)_4$, the residue $R^i$ being a branched or straight-chain alkyl radical with 1 to 4 C atoms. Zirconium alcoholates $Zr(OR^i)_4$ are preferred since especially good results are achieved with transesterification catalysts.

The literature discloses diverse transesterification catalysts, among others also those based on titanium and zirconium, for example from DE 199 42 541, Tetrahedron Lett. 1998, 39, 4223 and Synthesis 1982, 138. These transesterification catalysts can optionally be used in processes as claimed in the invention.

In one especially preferred process configuration as claimed in the invention, the initial mixture comprising bisabolol, farnesol and optionally other components is reacted with adipinic acid diisopropyl ester and zirconiumtetra-n-propylate. Outstanding results can be achieved with this combination.

The transesterification and esterification reaction is generally carried out at a temperature in the range of 100-250° C., preferably in the range of 150-200° C.

Reaction guidance under a weak vacuum, preferably at a pressure in the range of 500-10 mbar, is advantageous. In this connection typically the alcohol $R^1$—OH which forms in transesterification from the compound or compounds of formula B and optionally other low-boiling components (for example alcohols resulting from the transesterification catalyst) are distilled off.

In a final step, preferably at a pressure in the range of 0.5-5 mbar the desired product alpha-bisabolol is distilled by way of the head. The higher boiling products remain in the bottom, depending on the type and amount of compound(s) of formula B used, especially monocarboxylic acid farnesyl esters or dicarboxylic acid farnesyl esters and optionally unconverted amounts of compound(s) of formula B.

According to another aspect, the invention also relates to a process for producing a product which comprises alpha-bisabolol and which comprises the following steps:

conversion of nerolidol to a product mixture comprising alpha-bisabolol and farnesol, esterification of farnesol in the product mixture according to a process as claimed in the invention.

In this case, with respect to the preferred configuration of the process for esterification of the farnesol, the aforementioned applies accordingly.

The process (i) as claimed in the invention for esterification of farnesol in a mixture comprising alpha-bisabolol, farnesol and optionally other components and (ii) for producing a product comprising alpha-bisabolol are completed preferably by a processing/cleaning operation. Within the framework of the processing/cleaning operation the alpha-bisabolol and the ester formed by conversion of farnesol with the compound of formula B are preferably separated from one another.

One especially preferred processing/cleaning operation comprises the following steps:

distillative separation of the alpha-bisabolol from the reaction mixture from the transesterification reaction.

After separation of the alpha-bisabolol from the monocarboxylic acid farnesyl ester or dicarboxylic acid farnesyl ester/dicarboxylic acid alkyl farnesyl ester formed by conversion of the farnesol with the compound of formula B, the product formed does not comprise the indicated ester or esters and has a content of farnesol of less than 0.5% by weight. Typically, for example after carrying out fractionated distillation, the alpha-bisabolol is present in a high-purity form, as is desired by the cosmetics industry.

The invention will be explained below in greater detail with reference to the embodiments.

EXAMPLE 1

Production of Alpha-bisabolol (Not According to the Invention)

A standard apparatus consisting of a 2000 ml triple-neck flask with a reflux filter, droplet funnel and a thermometer is filled with 266 g (1.2 mole) (+/−) nerolidol and 528 g (9.1 mole) acetone. Then, at 10° C. a solution of 22 g (0.192 mole) methane sulfonic acid and 10.8 g (67 mmole) perchloric acid 60% was added dropwise within 30 minutes. Then the reaction mixture was stirred for 24 hours at 15° C. and processed after completed GC control.

Processing took place such that the reaction mixture was mixed with 500 g and 200 g diethylether and afterwards the organic phase was separated. The organic phase was washed neutral with soda solution and water. After distilling off the solvent 268 g of raw product remained.

GC: alpha-bisabolol 47.2%;

Farnesol (total of 4 isomers cis/cis; cis/trans; trans/cis; trans/trans): 2.4%

The raw product moreover comprised considerable amounts of nerolidol and farnesenes and other sesquiterpene hydrocarbons.

EXAMPLE 2

Production of Alpha-bisabolol (Not According to the Invention)

A 2000 ml triple-neck flask with a reflux filter, droplet funnel and a thermometer was filled with 264 g (1.2 mole) (+/−) nerolidol and 528 g (9.1 mole) acetone. Then, at 15° C. 10.8 g (67.2 mmole) 60% perchloric acid % was added dropwise within 40 minutes. Then the reaction mixture was restirred for 24 hours at 20° C. and processed after completed GC control.

Processing took place such that the reaction mixture was mixed with 500 g water and 200 g diethylether and afterwards the organic phase was separated. The organic phase was then washed neutral with soda solution and water. After distilling off the solvent, 272 g of raw product remained.

GC: alpha-bisabolol: 23.4%

Farnesol (total of 4 isomers cis/cis; cis/trans; trans/cis; trans/trans): 17.4%

Bisabolene (based on elimination from bisabolol): 55.4%

EXAMPLE 3.1

Production of Bisabolyl Formiate (not According to the Invention)

A 2000 ml triple-neck flask with a reflux filter and a thermometer was filled with 264 g (1.2 mole) (+/−) nerolidol and 100 g hexane. Then at a temperature of 10-15° C. a total of 92 g (2 moles) formic acid were added dropwise within 60 minutes. Then the reaction mixture was stirred for 20 hours at 10-15° C. and processed after completed GC control.

Processing was done such that the reaction mixture was mixed with 500 g water. Afterwards the organic phase was separated and washed neutral with soda solution and water. After distilling off the solvent, 300 g of raw product remained.

GC: alpha-bisabolyl formiate: 38.9%;

Farnesyl formiate (total of 4 isomers cis/cis; cis/trans; trans/cis; trans/trans): 29.7%

EXAMPLE 3.2

Production of Alpha-bisabolol (not According to the Invention)

A 2000 ml triple-neck flask with a reflux filter, droplet funnel and a thermometer was filled with 300 g (0.8 mole) raw mixture from example 3.1, and 400 g methanol, and then at a temperature of 20-40° C. mixed with 480 g 10% sodium hydroxide solution within 15 minutes. Then stirring continued for another 2 hours at 30-40° C. and processing was done after completed GC control.

Processing took place such that the reaction mixture was mixed with 400 g water and 200 g diethylether and afterwards the organic phase was separated. The organic phase was then washed neutral with water. After distilling off the solvent 259.2 g of raw product remained.
GC: alpha-bisabolol: 37.3%

Farnesol (total of 4 isomers cis/cis; cis/trans; trans/cis; trans/trans): 28.9%

The bisabolol content was increased to 86% and the farnesol content (c/c) was reduced to 7% by rectification on a 40-plate column.

EXAMPLE 4

Production of Farnesol-depleted Alpha-bisabolol (as Claimed in the Invention)

A 1000 ml triple-neck flask with a distillation bridge and a thermometer was filled with 500 g bisabolol/farnesol-mixture (86% bisabolol, 7% farnesol according to 0.16 mole farnesol), 50 g adipinic acid isopropyl ester (0.22 mole) and 5 g zirconium tetrapropylate (70% in propanol, corresponds to 0.01 mole) and at a temperature of 160-165° C. and a pressure of 30 mbar heated for 2 hours. 11 g of low-boiling components (propanol and isopropanol) are distilled over. The reaction mixture is then distilled on a 60 cm column with VABX packing at 1 mbar vacuum.

At a head temperature of 110-121° C. a total of 26 g of first runnings pass over.

At a head temperature of 121-122° C. 413 g of the main fraction pass over (GC: alpha-bisabolol 95.3%; <0.1% farnesol; this corresponds to a yield of 92% of the theoretical. In the reactor 86 g of a distillation residue remain which contains mainly difarnesyl adipate and isopropyl farnesyl adipate.

EXAMPLE 5

Production of Farnesol-depleted Alpha-bisabolol (as Claimed in the Invention)

A 1000 ml triple-neck flask with attached 30 cm packed column with V4A coils, distillation bridge and a thermometer was filled with 500 g bisabolol/farnesol-mixture (86% bisabolol, 7% farnesol according to 0.16 mole farnesol), 50 g benzoic acid methyl ester (0.37 mole) and 5 g zirconium tetrapropylate (70% in propanol, corresponds to 0.01 mole) and heated at a temperature of 160-165° C. and a pressure of 30 mbar for 2 hours. 10 g of low-boiling components (methanol and isopropanol) are distilled over. The reaction mixture is then distilled at 3 mbar.

At a head temperature of 110-126° C. 25 g of first runnings pass over.

At a head temperature of 126-135° C., 432 g of the main fraction pass over (GC: alpha-bisabolol 94.8%; 0.1% farnesol), this corresponds to a yield of 95% of the theoretical. In the reactor 80 g of a distillation residue remain which contains mainly isopropyl farnesyl BENZOATE.

The invention claimed is:

1. Process for esterification of farnesol in an initial mixture comprising alpha-bisabolol, farnesol and optionally other components, with the following steps:

(a) Preparation or production of the initial mixture, and
(b) addition of (i) a transesterification catalyst and (ii) one or more compounds of formula (B)

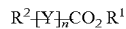

$$R^2\text{-}[Y]_n\text{-}CO_2R^1 \qquad B$$

in which the following applies
$R^1$ stands for an alkyl residue with 1 to 12 C atoms;
$R^2$ stands for hydrogen, an alkyl residue with 1 to 20 C atoms, a cycloalkyl residue with 5 to 20 C atoms, an aryl residue with 6 to 20 C atoms or a heteroaryl residue with 5 to 20 C atoms; and
Y stands for $CH_2$, $CH(Me)$, $CH(Et)$, $C(Me)_2$, $CH_2$—CH(Me), $CH(Me)$-$CH_2$ or $CH_2$—$CH(Me)$-$CH_2$ and n stands for a whole number from 0 to 6;
or
$R^2$ stands for a group $CO_2R^3$, $R^3$ standing for an alkyl residue with 1 to 12 C atoms; and
Y stands for $CH_2$, $CH(Me)$, $CH(Et)$, $C(Me)_2$, $CH_2$—CH(Me), $CH(Me)$-$CH_2$ or $CH_2$—$CH(Me)$-$CH_2$ and n stands for a whole number from 0 to 8, or
Y stands for an optionally substituted phenyl or naphthyl ring with a total of at most four substituents on the ring, n=1 applying.

2. The process as in claim 1, wherein the amount of one or more compounds of formula (B) which were used is preferably sufficient to esterify the amount of farnesol present in the mixture.

3. The process as in claim 1, wherein the molar ratio of farnesol to the total amount of compound or compounds of formula (B) is preferably in the range from 1:1 to 1:10, preferably in the range from 1:1.1 to 1:5.

4. The process as in claim 1, wherein one or more additional components selected from the group consisting of the following are present in the mixture: nerolidol, elimination products of bisabolol, elimination products of farnesol, elimination products of nerolidol, etherification products of farnesol, sesquiterpenes and sesquiterpene alcohols.

5. The process as in claim 1, wherein in formula (B) $R^1$ stands for an alkyl residue with 1 to 4 carbon atoms, especially preferably methyl, ethyl, n-propyl, or iso-propyl.

6. The process as in claim 1, wherein the compound of formula (B) is a monocarboxylic acid alkyl ester, and $R^2$ is preferably hydrogen, an alkyl residue with 3 to 8 C atoms or an aryl residue with 6 to 10 C atoms, especially preferably an aryl residue with 6 to 8 C atoms; and/or Y stands for $CH_2$, $CH(Me)$, $CH_2$—CH(Me), $CH(Me)$-$CH_2$ or $CH_2$—CH (Me)-$CH_2$ and n stands for a whole number from 0 to 6.

7. The process as in claim 1, wherein the compound of formula (B) is selected from the group consisting of benzoic acid-$C_1$—$C_4$-ester, especially benzoic acid methyl ester and benzoic acid ethyl ester.

8. The process as in claim 1, wherein the compound (B) constitutes a dicarboxylic acid dialkyl ester, $R^2$ stands for a group $CO_2R^3$, $R^3$ standing for an alkyl residue with 1 to 4 C atoms, especially methyl, ethyl, n-propyl, or iso-propyl, and/or
Y stands for $CH_2$ and n stands for a whole number from 0 to 6, preferably a whole number from 2 to 5, or
Y stands for $CH_2$—CH(Me), $CH(Me)$-$CH_2$ or $CH_2$—CH (Me)-$CH_2$ and n =0, 1 or 2; or
Y stands for a phenyl or naphthyl ring, n being equal to 1.

9. The process as in claim 1, wherein the compound according to formula (B) is selected from the following: succinic acid-$C_1$-$C_4$-ester, especially succinic acid ethyl ester, succinic acid isopropyl ester, adipinic acid-$C_1$-$C_4$-ester, especially adipinic acid ethyl ester, adipinic acid isopropyl ester, glutaric acid-$C_1$-$C_4$-ester, especially glutaric acid acid ethyl ester, glutaric acid isopropyl ester, 3-methylglutaric acid-$C_1$-$C_4$-ester, especially 3-methylglutaric acid acid ethyl ester, 3-methylglutaric acid isopropyl ester, subaric acid-$C_1$-$C_4$-ester, azelaic acid-$C_1$-$C_4$-ester.

10. The process as in claim 1, wherein the compound according to formula (B) is selected from the group consisting of phthalic acid diethyl ester, phthalic acid diisopropyl ester, phthalic acid dibutyl ester, terephthalic acid diethyl ester, 2,6-naphthalinic dicarboxylic acid diethyl ester, 2,6-naphthalinic dicarboxylic acid di-2-ethylhexylester.

11. Process for producing a product comprising alpha-bisabolol, with the following steps:
   conversion of nerolidol into a mixture comprising alpha-bisabolol and farnesol,
   esterification of farnesol in the product mixture according to a process as claimed in claim 1.

12. The process as in claim 11, wherein the molar ratio of farnesol to the compound of formula (B) are separated from one another.

13. The process as in claim 11, furthermore comprising the following step:
   distillative separation of the alpha-bisabolol from the reaction mixture.

14. The process as in claim 1, wherein the transesterification catalyst comprises a titanium alcoholate $Ti(OR^i)_4$ and/or a zirconium alcoholate $Zr(OR^i)_4$, where $R^i$ represents a branched or straight-chain alkyl residue with 1 to 12 C atoms.

* * * * *